(12) United States Patent
Kern

(10) Patent No.: US 7,184,517 B2
(45) Date of Patent: Feb. 27, 2007

(54) ANALYTICAL METHOD FOR DETERMINATION OF CRYSTALLOGRAPHIC PHASES OF A SAMPLE

(75) Inventor: Arnt Kern, Woerth (DE)

(73) Assignee: Bruker AXS GmbH, Karlsruhe (DE)

( * ) Notice: Subject to any disclaimer, the term of this patent is extended or adjusted under 35 U.S.C. 154(b) by 68 days.

(21) Appl. No.: 10/952,823

(22) Filed: Sep. 30, 2004

(65) Prior Publication Data

US 2005/0074089 A1    Apr. 7, 2005

(30) Foreign Application Priority Data

Oct. 7, 2003    (DE) ............................... 103 46 433

(51) Int. Cl.
*G01N 23/00* (2006.01)
*G01N 23/207* (2006.01)
*G01N 23/223* (2006.01)

(52) U.S. Cl. ........................... 378/90; 378/46; 378/73; 378/83

(58) Field of Classification Search ................ 378/45, 378/46, 47, 48, 49, 71, 73, 83, 90, 210
See application file for complete search history.

(56) References Cited

U.S. PATENT DOCUMENTS

| | | | | |
|---|---|---|---|---|
| 5,406,608 A * | 4/1995 | Yellepeddi et al. | ............ | 378/46 |
| 5,414,747 A * | 5/1995 | Ruud et al. | ................... | 378/73 |
| 5,442,676 A * | 8/1995 | Fewster | ........................ | 378/72 |
| 6,577,705 B1 * | 6/2003 | Chang et al. | ................. | 378/45 |
| 6,798,863 B2 * | 9/2004 | Sato | ............................ | 378/46 |
| 6,885,727 B2 * | 4/2005 | Tamura | ....................... | 378/45 |

2002/0097834 A1    7/2002    Satoh

FOREIGN PATENT DOCUMENTS

| | | |
|---|---|---|
| JP | 083 34 481 | 12/1996 |
| JP | 100 82 749 | 3/1998 |

OTHER PUBLICATIONS

"New software expands the role of industrial X-ray analysis", Roger Meier and Mark Dirken, International Cement & Lime Journal, 2, 2002, p. 18 ff.
"Interactive process control with new ultra-fast industrial X-ray diffraction systems", Roger Meier and Mark Dirken, International Cement & Lime Journal, 1, 2002, p. 44 ff
G.S. Pawley "Unit- Cell Refinement . . . " J. App. Cryst. (1981) 14, 357-361. .

(Continued)

*Primary Examiner*—Edward J. Glick
*Assistant Examiner*—Anastasia S. Midkiff
(74) *Attorney, Agent, or Firm*—Paul Vincent

(57) ABSTRACT

An analytical method for determining crystallographic phases of a measuring sample comprises the steps of acquiring a diffraction pattern of the measuring sample and qualitative phase analysis of the measured diffraction pattern, acquiring an element spectrum of the measuring sample and determining concentrations of chemical elements in the measuring sample from the acquired element spectrum, and carrying out a quantitative phase analysis of the measuring sample on the basis of the measured intensities of the acquired diffraction pattern thereby taking into consideration determined element concentrations as a boundary condition, wherein differences between calculated and measured intensities of the diffraction pattern and between calculated and determined element concentrations are simultaneously minimized in an iterative process. The inventive method permits quantitative phase determination with high reliability.

16 Claims, 1 Drawing Sheet

OTHER PUBLICATIONS

A. Lebail, Extracting Structure Factors . . . , Accuracy in Powder Diffraction II, Proc. Int. Conf. 1992, NIST Special Publication 846, E. Prince and J.K. Stalick, Editors, p. 213.

H.M. Rietveld, "A Profile Refinement Method . . . ," J. Appl. Cryst. (1969), 2, 65.

R.C. Jones, C.J. Babcock, W.B. Knowlton: "Estimation of the Total Amorphous Content of Hawai's Soils by the Rietveld Method" Soil Science Society of America Journal, vol. 64, May 2000, pp. 1100-1108, XP002315898 *Abstract* *p. 1102-p. 1105*.

A. Carreas, R. Bonetto, G. Stutz et al: "Parameter refinement in the analysis of X-ray irradiated samples" X-Ray Spectrometry, vol. 31, No. 2, Mar. 2002, pp. 173-177, XP002315899 *entire document*.

D. Bish et al: "Application of the Chemin XRD/XRF" Online! 1997, XP002315900 Internet: URL:www.lpi.usra.edu/meetings/earlymars/pdf/3002.pdf> 'on Feb. 1, 2005! *p. 1, left Col.* *p. 2, left Col.*.

R. Bonetto, G. Castellano, J. Trincavelli: "Optimization of parameters in electron probe microanalysis" X-Ray Spectrometry, vol. 30, No. 5, Sep. 2001, pp. 313-319, XP002315901 *Abstract* *p. 313, left Col.*.

* cited by examiner

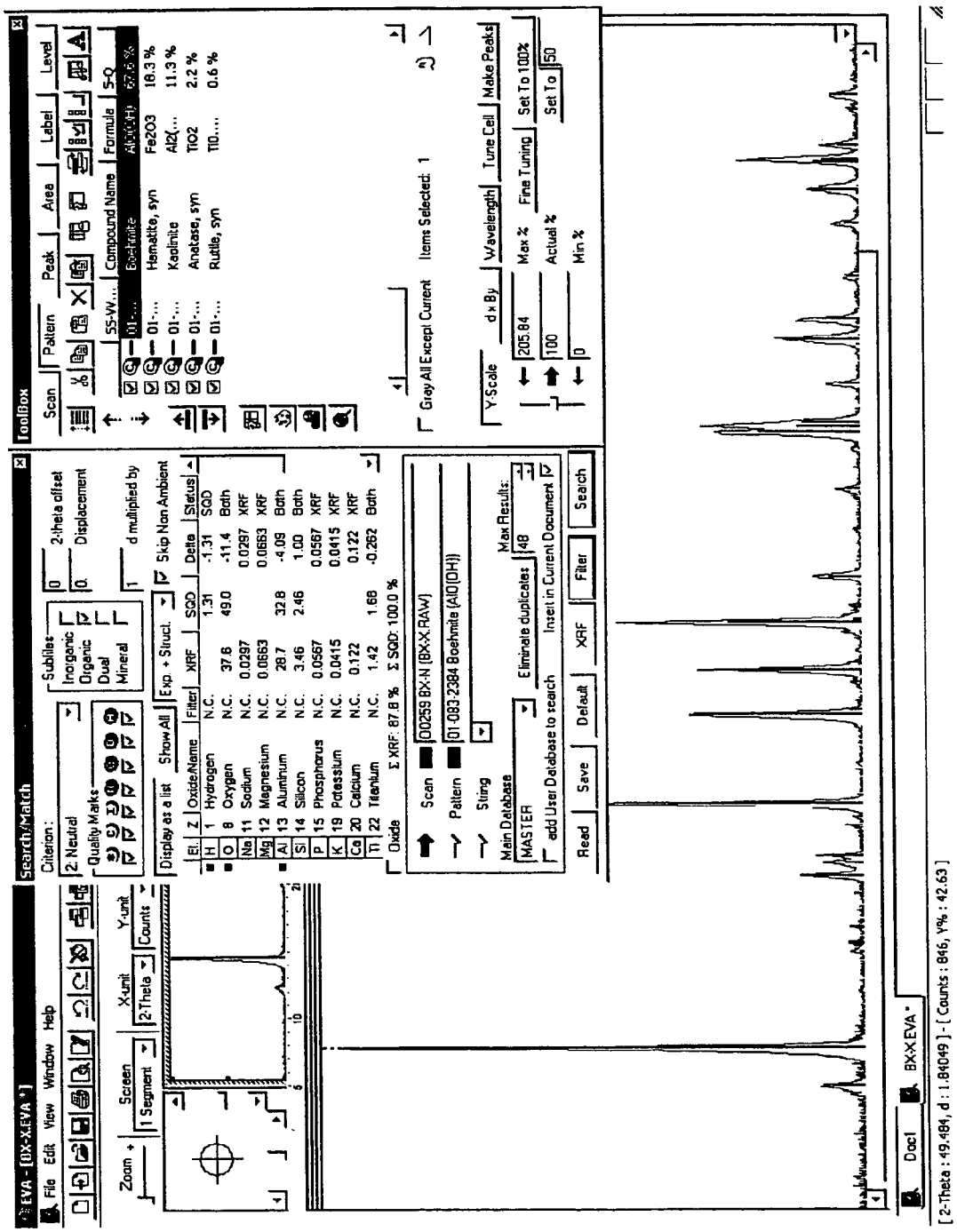

ANALYTICAL METHOD FOR DETERMINATION OF CRYSTALLOGRAPHIC PHASES OF A SAMPLE

This application claims Paris Convention priority of DE 103 46 433.6 filed Oct. 07, 2003 the complete disclosure of which is hereby incorporated by reference.

BACKGROUND OF THE INVENTION

The invention concerns an analytical method for determining crystallographic phases of a measuring sample, wherein a diffraction pattern of the measuring sample and an element spectrum of the measuring sample are acquired.

A method of this type is disclosed in R. Meier and M. Dirken, International Cement & Lime Journal, Issue 2 (2002), pages 18–21.

Information about crystallographic phases in a measuring sample can be obtained with diffraction experiments, such as e.g. X-ray diffraction (XRD), electron diffraction or neutron diffraction. Towards this end, a focussed or paralleled, essentially monochromatic beam of X-rays, electrons, or neutrons is directed onto the measuring sample and the diffracted beam (or the diffracted rays) is registered by a detector. The position of the diffracted rays provides information concerning the qualitative composition of the measuring sample, and the intensity provides information concerning the portion (concentration) of the respective phases.

Qualitative and quantitative analysis using diffraction experiments may be complicated by the type of measuring sample. In particular, foreign atom portions in crystals (doping) are difficult to recognize in the diffraction spectrum and amorphous sample portions or multiple scattering may also falsify the analysis.

To facilitate the qualitative analysis of measuring samples, an element spectrum of the measuring sample is conventionally acquired, e.g. using X-ray fluorescence (XRF) (compare R. Meier cit. loc.). Phases which would require chemical elements which are not detected in the sample can be omitted in the qualitative phase analysis using information concerning the element concentrations in the sample. Use of the element spectrum increases the reliability of the qualitative phase analysis of the diffraction spectrum. Only the phases selected in the qualitative phase-analysis are then included in the quantitative phase analysis of the diffraction spectrum.

In this conventional analytical method, the result of the quantitative phase analysis of the diffraction pattern is often quantitatively incompatible with the measured element concentrations determined from the element spectrum. Determination of the phase portions of the crystallographic phases from the diffraction pattern is therefore incorrect.

Departing therefrom, it is the object of the present invention to provide a more reliable quantitative phase analysis of a measuring sample.

SUMMARY OF THE INVENTION

This object is achieved in accordance with the invention with an analytical method for determining crystallographic phases of a measuring sample which comprises the following steps:

(a) acquisition of a diffraction pattern of the measuring sample and qualitative phase analysis on the basis of the measured diffraction pattern;

(b) acquisition of an element spectrum of the measuring sample and determination of the measured concentrations of chemical elements in the measuring sample from the acquired element spectrum;

(c) carrying out a quantitative phase analysis of the measuring sample on the basis of the measured intensities of the acquired diffraction pattern thereby taking into consideration the element concentrations determined in step (b) as boundary conditions, wherein the differences between the calculated and measured intensities of the diffraction pattern and between the calculated and determined element concentrations are simultaneously minimized in an iterative process.

In accordance with the inventive method, a second set of constraints (boundary conditions) are introduced into the quantitative analysis of the diffraction pattern: namely, the concentrations of the chemical elements contained in the measuring sample which were determined via the element spectrum. If an assumed (i.e. initially assumed) phase composition is examined within the scope of the quantitative phase analysis, two values must be optimized in accordance with the invention. Initially, a diffraction pattern or parts of a diffraction pattern (e.g. individual reflex maxima) are calculated from the assumed phase composition and a first difference value is determined from a comparison to the measured diffraction pattern. Moreover, element concentrations calculated from the assumed phase composition are determined and a second difference value is determined from a comparison to the measured element concentrations in accordance with the element spectrum. The correspondence between the assumed phase composition and the actual phase composition of the measuring sample is assessed on the basis of the first and second difference values. As a result of the quantitative phase analysis, from the plurality of assumed phase compositions, that phase composition is determined which has the lowest first and second difference values.

Calculation of the diffraction pattern (or parts of the diffraction pattern) from the assumed phase composition of the measuring sample may be effected through ab-initio simulation (i.e. within the scope of a Rietveld analysis) or through extrapolation of a diffraction pattern available in a database or stick pattern of the assumed relative phase concentration. The latter calculation method is fast and can also be used for phases of unknown atomic structure.

The first and second difference values may be weighted differently. The two difference values are preferably identically weighted such that both difference values change by the same amount in response to an infinitesimal change of one individual phase portion. Alternatively, the second difference value may be weighted to such an extent as to rule out assumed phase compositions which result in a deviation of the calculated element concentration from the measured element concentration which is larger than the measuring inaccuracy of the element spectrum. In this case, the measured element concentration is considered to be true and the concentrations of various crystallographic phases in the measuring sample are strictly correlated thereto.

The inventive method is particularly suited for a quantitative analysis of mixtures of a plurality of phases, wherein the individual phases contain large portions of identical elements. In this case, the second difference value is a second constraint which considerably reduces the possible phase compositions.

The inventive method may be performed with particular advantage using a data processing system (computer) and a suitable computer program (software), wherein the data processing system is preferably connected to a suitable measuring device or suitable measuring devices for acquisition of the diffraction pattern and/or of the element spectrum of the measuring sample. For this reason, a computer program for carrying out the inventive analytical method is also part of the present invention.

In one particularly preferred method variant, in step (c), reference data is interactively adjusted to observed reflex maxima of the acquired diffraction pattern, wherein the adjustment is preferably manually and/or graphically based. Software provides e.g. a stick pattern of reflex maxima of the assumed phases of the assumed phase composition of the measuring sample in view of the measured diffraction pattern, and a user adjusts the assumed phase composition by newly scaling one of the stick patterns, i.e. changes a relative concentration of a phase. The stick patterns of the other phases are preferably automatically adjusted thereby observing the second constraint of the element concentrations. The user can monitor the assessment of the diffraction pattern and element spectrum with this method thereby largely directly interpreting the measured information. Alternatively, fully automatic method variants are also possible.

In a further development of this method variant, the adjustment is carried out using a minimizing algorithm, in particular, the value $$Chi^2 = \sum_{i=1}^{M} w_i [Imax_i(\text{obs}) - Imax_i(\text{calc})]^2 + \sum_{e=1}^{N} [w_e E(\text{obs}) - E(\text{calc})]^2$$

is minimized, wherein
  $Imax_i(\text{obs})$: observed reflex maximum
  $Imax_i(\text{calc})$: calculated reflex maximum
  $E(\text{obs})$: observed element concentration
  $E(\text{calc})$: calculated element concentration
  M: maximum number of reflex maxima used
  i: count variable of the reflex maxima
  N: maximum number of elements used
  e: count variable of the elements
  $w_i$: weighting factor
  $w_e$: scaling constant.

The minimizing value contains the deviations between calculated and observed diffraction pattern (first difference value) and the deviations between the calculated and measured element concentrations (second difference value). Any reflex maximum and any element can basically be associated with a weighting factor. The value $Chi^2$ can easily be fully automatically minimized for rapid determination of the phase composition of the sample. It should be observed that the peak value of the intensity spectrum, and also an integral intensity in the vicinity of the peak value can preferably be used as a numerical value of a reflex maximum.

In another further development of the method variant, the adjustment is carried out on the basis of all observed measuring points of the diffraction pattern of the measuring sample, in particular, through quantitative Rietveld analysis (e.g. in accordance with H. M. Rietveld, Acta Cryst. 22 (1967), 151–152; H. M. Rietveld, J. Appl. Cryst. 2 (1969), 65–71) or independent of crystal-structure "Full Pattern Matching Methods" (e.g. in accordance with Le Bail et al., Mat. Res. Bull. 23 (1988), 447–452; G. S. Pawley, J. Appl. Cryst. 14 (1981), 357–361) or with a combination of Rietveld analysis and crystal-structure independent "Full Pattern Matching" methods. The use of all measuring points of the diffraction pattern broadens the basis of the quantitative analysis, rendering it more reliable through reduction of problems due to reflex overlaps.

This further development may be augmented in a method variant in accordance with the invention, with which adjustment is carried out by means of a minimizing algorithm, in particular, with the value $$Chi^2 = \sum_{i=1}^{M} w_i [Y_i(\text{obs}) - Y_i(\text{calc})]^2 + \sum_{e=1}^{N} [w_e E(\text{obs}) - E(\text{calc})]^2$$

being minimized, wherein:
  $Y_i(\text{obs})$: observed measuring point
  $Y_i(\text{calc})$: calculated measuring pint
  $E(\text{obs})$: observed element concentration
  $E(\text{calc})$: calculated element concentration
  M: maximum number of measuring points used
  i: count variable of the measuring points
  N: maximum number of elements used
  e: count variable of the elements
  $w_i$: weighting factor
  $w_e$: scaling constant.

A minimizing algorithm of this type objectifies determination of the optimum correspondence between calculated and measured data and facilitates automatic determination of this optimum correspondence.

In one particularly preferred variant of the inventive method, the diffraction pattern of an X-ray diffraction (XRD) diagram and the element spectrum is an X-ray fluorescence (XRF) spectrum. XRD and XRF are non-destructive examination methods which are inexpensive to carry out and require little or no sample preparation.

In one embodiment of this method variant, the XRD and XRF measurements are advantageously carried out in a combined apparatus. This optionally reduces the amount of measuring equipment, avoids sample change and can reduce the measurement paths. Moreover, the required data for the inventive method is provided by one apparatus, which simplifies compatibility of the measuring data, data formatting, and data import to a computer.

In a preferred method variant, solutions are rejected in step (a) which would require the presence of elements in the measuring sample which are not proven in the element spectrum of step (b). This facilitates the qualitative analysis. This measure is known per se in the art in connection with qualitative analysis.

In another advantageous variant of the inventive method, the method is used for quality control, in particular, online. The high reliability of the inventive quantitative analysis and good automation permits monitoring of strict quality standards in substantially real time.

In one preferred method variant, the measuring sample comprises an inorganic sample, e.g. a concrete sample and/or a ceramic sample and/or a rock sample. The inventive method can be used with particular efficiency for samples having a high crystalline fraction, since the measured diffraction pattern contains a particularly large amount of information.

Further advantages of the invention can be extracted from the description and the drawing. The features mentioned above and below may be used in accordance with the invention individually or collectively in arbitrary combination. The embodiments shown and described are not to be understood as exhaustive enumeration but have exemplary character for describing the invention.

The invention is shown in the drawing and is explained in more detail with reference to an embodiment.

BRIEF DESCRIPTION OF THE DRAWING

The FIGURE shows a display screen image of software for carrying out the inventive analytical method.

DESCRIPTION OF THE PREFERRED EMBODIMENT

The inventive method initially starts with acquisition of an element spectrum (e.g. XRF) and acquisition of a diffraction pattern (e.g. XRD) of a measuring sample. The results of these two measurements are used in the inventive method to carry out a quantitative determination of the concentration of the phases contained in the measuring sample, with high reliability and accuracy. At least the second part of the inventive method is performed with the assistance of software on a computer. This software may already have controlled acquisition of the element spectrum and the diffraction pattern or can be linked to the associated control software. Alternatively, the results of the acquisitions are imported into the software, e.g. as text files, via a disc.

The acquisitions are evaluated in accordance with the following steps:

1. Loading a diffraction pattern, e.g. an XRD measurement into the computer and loading of an element spectrum or element concentrations, which may also be effected after step 2.

2. Performance of a qualitative analysis of the diffraction pattern e.g. by means of the PDF database of the ICDD (International Centre for Diffraction Data) or a user-defined database. So-called patterns (i.e. sets of plane separations d versus intensities of a phase) are thereby identified which come closest to the measured diffraction pattern. The qualitative analysis may be effected automatically (search/match function) or through manual selection, i.e. when the crystallographic phases in the measuring sample are known, e.g. in consequence of sample production. The search/match function can be limited to phases which only contain elements detected in the element spectrum. The user can also manually predetermine the allowed elements.

The phases found in the qualitative analysis are preferably represented as so-called stick patterns and are mixed into the measured diffraction pattern. A stick pattern thereby comprises the diffraction reflexes of the detected phase with an intensity ratio which is characteristic for the phase. The stick patterns of different phases are preferably represented by different colors.

The lower part of the FIGURE shows a measured diffraction pattern, towards the right, the diffraction angle (2 theta) and towards the top, the intensity. The measured reflex maxima are each superimposed with sticks which approximate the angular position and intensity of the respective reflex maxima. The right upper part of the FIGURE shows a window tool box which lists the detected phases. Each detected phase is associated with a stick pattern (which each comprises several sticks) in the diffraction pattern.

Association of an absolute intensity to the stick patterns (and thereby determination of the concentration of the phase in the measuring sample) can initially be omitted within the scope of the qualitative analysis.

Concerning qualitative phase analysis, reference is also made to R. Jenkins, R. L. Snyder, Introduction to X-ray Powder Diffractometry. Chemical Analysis, Vol. 138 (1996), Wiley-Interscience.

3. The above is followed by a quantitative phase analysis, i.e. determination of the relative portion of the individual detected phases in the measuring sample by minimizing the differences between calculated and measured intensities of the diffraction pattern as well as between calculated and determined element concentrations, in an iterative manner. In the simplest case, the phase portions are adjusted in a manual, graphic manner.

The upper central part of the FIGURE shows the window search/match. This window contains a list of elements which are associated with a concentration value on the basis of the element spectrum in the list "XRF". The list contains all elements detected in the sample by means of the element spectrum, as well as further elements which cannot be accessed with the element spectrum, but which are assumed to be in the sample (e.g. hydrogen in the case of XRF). Adjacent thereto is a list "SQD" which shows the concentrations of the elements—calculated in accordance with a presently assumed composition of the measuring sample from certain portions of phases (assumed phase composition). The column "delta" shows the difference between the columns "XRF" and "SQD". Concentrations are preferably stated in substance amounts %, alternatively also in weight %.

At the beginning of the adjustment, any assumed phase composition may be set, wherein the initial assumed phase adjustment is preferably oriented towards the absolute intensities of the reflex maxima in the diffraction pattern. The user can change the portion of individual phases in the window toolbox by marking the respective phase in the list and setting it with a slider (left bottom in the toolbox window). The other phases are preferably adjusted automatically such that, in total, 100% phase portions are allocated. The respective relative phase portions can be extracted from the column "S-Q" in the toolbox window. In this slider adjustment, the user can observe the difference in the element concentrations in the window search/match, column delta, and observe the difference in the diffraction pattern on the basis of stick lengths in comparison with the measured reflex maxima.

The user attempts to adjust the assumed phase composition of the measuring sample, such that the stick patterns only differ from the measured diffraction pattern by a minimum amount, i.e. the relative intensities of all sticks of all detected phases properly correspond to the relative intensities of the corresponding reflex maxima of the measured diffraction pattern. Moreover, one strives to obtain a minimum deviation of the calculated element concentrations in the assumed phase composition from the measured element concentration in accordance with the element spectrum.

The two deviations can be simultaneously minimized by the user through trial and error. To simplify determination of the amount of deviation, the two deviations can be associated with mathematically determinable difference values. These difference values may e.g. be represented on a monitor to support the user in adjusting the phase composition. It is also possible in accordance with the invention to calculate a matrix of many possible phase compositions and automatically determine a minimum of the difference values.

Towards this end, a conventional error value can be used i.e. as sum of the two difference values. One example of a conventional error value is $Chi^2$, as was defined above. The individual difference values can thereby be weighted in a fundamentally arbitrary fashion. Preferably, correspondence of the calculated and measured element concentrations is stringently required. This is particularly useful when an amorphous sample portion can be excluded (or neglected) in the measuring sample or an amorphous sample portion in the diffraction pattern is considered whose composition is exactly known.

In another variant of the inventive analytical method, a complete diffraction pattern is simulated through an ab initio calculation on the basis of the atomic structures of the individual phases from an assumed phase composition of the measuring sample (Rietveld method in a narrow sense, compare R. A. Young, The Rietveld Method, Oxford, Science Publications, 1993). The correspondence between the simulated and measured diffraction pattern can then be effected through determination of a covariance. In accordance with the invention, only those phase compositions are considered whose associated elementary composition corresponds to the measured element concentrations in the element spectrum. This considerably limits the matrix of possible phase compositions in the simulation, such that determination of the best phase composition is much quicker than without this second constraint. The result of the Rietveld determination must also always be compatible with the measured element spectrum in order to preclude unreasonable (and thereby unnecessary) Rietveld determinations in the result.

I claim:

1. An analytic method for determining crystallographic phases of a measuring sample, the method comprising the steps of:
    (a) acquiring an X-ray diffraction intensity pattern of the measuring sample and qualitatively phase analyzing the sample using the measured diffraction pattern intensities;
    (b) acquiring an element X-ray spectrum of the measuring sample and determining measured concentration of chemical elements in the measuring sample from the acquired element spectrum;
    (c) calculating an X-ray diffraction intensity pattern of the measuring sample;
    (d) calculating an X-ray element concentration spectrum of the measuring sample; and
    (e) quantitatively phase analyzing the measuring sample using measured intensities of the acquired diffraction pattern thereby taking into consideration the element concentrations determined in step (b) by simultaneously and iteratively minimizing differences between the calculated and the measured X-ray diffraction intensity patterns and between the calculated and the measured X-ray element concentration spectra.

2. The method of claim 1, wherein in step (e), interactive adjustment of the calculated X-ray diffraction intensity pattern to observed maxima of the acquired diffraction pattern is carried out.

3. The method of claim 2, wherein the adjustment is carried out manually or graphically.

4. The method of claim 2, wherein the adjustment is carried out by means of a minimizing algorithm.

5. The method of claim 4, wherein a value:

$$Chi^2 = \sum_{i=1}^{M} w_i[Imax_i(\text{obs}) - Imax_i(\text{calc})]^2 + \sum_{e=1}^{N} [w_e E(\text{obs}) - E(\text{calc})]^2$$

is minimized, wherein
    $Imax_i(\text{obs})$: observed reflex maximum
    $Imax_i(\text{calc})$: calculated reflex maximum
    $E(\text{obs})$: observed element concentration
    $E(\text{calc})$: calculated element concentration
    M: maximum number of reflex maxima used
    i: count variable of the reflex maxima
    N: maximum number of elements used
    e: count variable of the elements
    $w_i$: weighting factor
    $w_e$: scaling constant.

6. The method of claim 2, wherein the adjustment is carried out using all observed measuring points in the diffraction pattern of the measuring sample.

7. The method of claim 6, wherein a quantitative Rietveld analysis, a crystal-structure independent "full pattern matching" method, or a combination of Rietveld analysis and crystal-structure independent "full pattern matching" method is performed.

8. The method of claim 6, wherein the adjustment is carried out by means of a minimizing algorithm.

9. The method of claim 8, wherein a value:

$$Chi^2 = \sum_{i=1}^{M} w_i[Y_i(\text{obs}) - Y_i(\text{calc})]^2 + \sum_{e=1}^{N} [w_e E(\text{obs}) - E(\text{calc})]^2$$

is minimized, wherein
    $Y_i(\text{obs})$: observed measuring point
    $Y_i(\text{calc})$: calculated measuring pint
    $E(\text{obs})$: observed element concentration
    $E(\text{calc})$: calculated element concentration
    M: maximum number of measuring points used
    i: count variable of the measuring points
    N: maximum number of elements used
    e: count variable of the elements
    $w_i$: weighting factor
    $w_e$: scaling constant.

10. The method of claim 1, wherein the element spectrum is an X-ray fluorescence (XRF) spectrum.

11. The method of claim 10, wherein the X-ray diffraction pattern and XRF measurements are carried out in a combined apparatus.

12. The method of claim 1, wherein in step (a), solutions are rejected which would require a presence of elements in a measuring sample which are not detected in the element spectrum of step (b).

13. The method of claim 1, further comprising the step of categorizing the measuring sample as acceptable or unacceptable for quality control of a plurality of measured samples.

14. The method of claim 13, wherein the quality control is performed in real time.

15. The method of claim 1, wherein an inorganic sample is analysed.

16. The method of claim 15, wherein the sample comprises one of concrete, ceramic, and rock.

* * * * *